(12) United States Patent
Mehrgan

(10) Patent No.: US 11,986,432 B2
(45) Date of Patent: May 21, 2024

(54) PROPHYLACTIC AND INTIMACY AID DEVICE

(71) Applicant: Behrang Mehrgan, West Vancouver (CA)

(72) Inventor: Behrang Mehrgan, West Vancouver (CA)

(*) Notice: Subject to any disclaimer, the term of this patent is extended or adjusted under 35 U.S.C. 154(b) by 221 days.

(21) Appl. No.: 16/371,061

(22) Filed: Mar. 31, 2019

(65) Prior Publication Data

US 2022/0096316 A1    Mar. 31, 2022

(51) Int. Cl.
  *A61H 19/00*   (2006.01)
  *A61F 6/06*   (2006.01)
  *A61F 6/04*   (2006.01)

(52) U.S. Cl.
  CPC ............ *A61H 19/50* (2013.01); *A61F 6/065* (2013.01); *A61H 19/32* (2013.01); *A61H 19/34* (2013.01); *A61F 2006/041* (2013.01); *A61H 2205/087* (2013.01)

(58) Field of Classification Search
  CPC ........ A61H 19/50; A61H 19/32; A61H 19/34; A61H 2205/087; A61F 6/065; A61F 2006/041
  See application file for complete search history.

(56) References Cited

U.S. PATENT DOCUMENTS

| | | | |
|---|---|---|---|
| 2006/0042639 A1* | 3/2006 | Wallace | A61F 6/065 128/830 |
| 2014/0202468 A1* | 7/2014 | Parsi | A61F 6/04 128/845 |
| 2019/0021902 A1* | 1/2019 | Rhodes | A61F 6/065 |
| 2021/0251843 A1* | 8/2021 | Rivera | A61F 5/451 |

* cited by examiner

*Primary Examiner* — Steven O Douglas

(57) ABSTRACT

A multi-purpose wearable prophylactic and intimacy aid device made of a material mimicking human flesh, used during a sexual relationship having different purposes such as but not exclusive to providing, independently or in combination with a body part of the wearer at least one entryway to receive a means of penetration, reducing skin to skin contact to decrease the risk of STDs, and enhancing the size and shape of parts of the body of the wearer.

12 Claims, 12 Drawing Sheets

PROPHYLACTIC AND INTIMACY AID DEVICE

References Cited:

| | | |
|---|---|---|
| U.S. Pat. No. 4,794,920 | Jan. 3, 1989 | David M. |
| U.S. Pat. No. 4,862,901 | Sep. 5, 1989 | Ivan L. Green |
| U.S. Pat. No. 4,955,392 | Sep. 11, 1990 | Reuben Sorkin |
| U.S. Pat. No. 5,083,414 | Jan. 28, 1992 | Cheng M. |
| U.S. Pat. No. 5,181,527 | Jan. 26, 1993 | James C. |
| U.S. Pat. No. 5,413,117 | May 9, 1995 | Marquita Wills |
| U.S. Pat. No. 5,535,757 | Jul. 16, 1996 | Fleming Jr. |
| WO2001015624A2 | Mar. 8, 2001 | Carlos Solis |
| US2005/0087193A1 | Apr. 28, 2005 | Sylvia Scott |
| US2007/0193586A1 | Aug. 23, 2007 | Grace Elizabeth Vaughn |
| US2013/0160774A1 | Jun. 27, 9 2013 | Robert J. SCHUMAN |
| US20150128958A1 | May 14, 2015 | Chintan M Shah |
| US2016/0374850A1 | Dec. 29, 2016 | Arif H. Agha |
| US2017/0042726A1 | Feb. 16, 2017 | Carolyn Palmer |
| US2019/0021902A1 | Jan. 24, 2019 | James Rhodes |

BACKGROUND OF THE INVENTION

1. Field of Invention

The present invention discloses wearable devices and solutions for couples aimed to enhance both the protection and quality of sexual activities, making use of such devices more physically and visually attractive for the users, thus help reducing the risk of STD.

2. Description of the Related Art

The sex dolls and sex robots industries have been evolving rapidly in the recent years. The sex robots and sex dolls now seem much more attractive and realistic both to the eye and the body. However, they are still not real. The present invention has the intention to employ the advancements of manufacturing sex dolls/robots, for using wearables those actually mimic living body parts of the wearer to be used independently or in combination with actual body parts of the wearer.

Wearing butt pads, silicon padded underwear, hip enhancer pads, padded bras and similar products to shape buttocks, hips, legs, and breasts is very common for cosmetic reasons. While such products are mainly worn under the dress of the wearer, the present invention suggests making similarly shaped wearable pieces made of materials mimicking human flesh and skin such as the ones used in sex doll industry both under the dress and during a sexual relationship.

Such products may have cavities, orifices, cleavages, grooves, valleys, depressions, etc. those independently or in combination with the wearers' body parts simulate cleavages or orifices such as but not exclusive to anus, vagina, mouth, throat, breasts cleavage and help to simulate sexual activities such as but not limited to sexual intercourse, mammary intercourse, intergluteal sex, intercrural sex, axillary intercourse, hand job, foot job, etc.

There may be occasions when a person has the intention to get engaged in a sexual activity with a male partner but for personal, religious, medical, hygiene reasons, or physical reasons or limitations does not have the intention or the possibility to have at least one kind of sexual activity such as a sexual intercourse, oral sex, anal sex, mammary intercourse, intercrural sex, interglutal sex, etc. with said partner. Said reasons, conditions or limitations may include but not limited to menstruation, virginity, medical conditions, pregnancy, post-surgery, after or during cancer treatments, injury, size and shape of body parts (e.g. having small breast), being in the early stages of a relationship, personal dislikes, beliefs, preferences, gender, etc. The present invention may be a relationship saver in such situations by providing a natural feeling solution to mimic such sexual activities.

Patent No. US2017/0042726 A1 dated Feb. 16, 2017 by Carolyn Palmer provides a similar approach by attaching a receiver apparatus acting as a female orifice to a garment worn by a user. The main disadvantage of this approach is that the receiver apparatus is a redundant member and does not feel like a natural body part. For instance, in occasions that it gets positioned between two users, it feels uncomfortable to both partners. It also needs a heater to adapt to the body temperature of the wearer since is mounted on the outer surface of a garment. The present invention however, not only acts as an expansion to the body of the wearer, but also may be worn hours before a sexual activity, directly on the body of the wearer and under the dress. So it perfectly adapts to the body temperature of the user.

Patent No. US2019/0021902 A1 dated Jan. 24, 2019 by James Rhodes provides a solution for the similar purpose comprising a condom which is attached inside a garment to be used as a sheath for penetration, while its closed end is attached to a place out of the body of the wearer to guaranty that no intercourse can occur.

While condoms help reduce the risk of Sexually Transmitted diseases (STD), they are not effective against some diseases and infections such as HPV since condoms do not provide any protection against skin to skin contact in areas such as pubic area, scrotum, upper thigh, and upper groin. The present invention provides solutions to eliminate such contacts during sexual activities. Some implementations of the present invention also eliminate every type of contact and can 100% eliminate the risk of STD and STI.

Patent No. US20150128958A1 dated May 14, 2015 by Chintan M Shah provides a solution to cover the pubic area of the female wearer. Patent No. US2016/0374850A1 dated Dec. 29, 2016 by Arif H. Agha, provides an adhering pubic area shield. U.S. Pat. No. 5,413,117 dated May 9, 1995 by Marquita Wills provides a pubic area shield with a sealing/wiping orifice at the genital area. All three patents are suggested to be used together with a male condom in order to be effective against STD. Wearing a female garment having an orifice at the genital area together with a male partner using a male condom is assumed to reduce the probability of transfer of diseases. But these solutions cannot really be effective against STD/STI. The first said two patents do not prevent the bodily fluid of the female user at all from coming out of the orifice and smearing the outer surface of the latex garment/shield, which can transfer infection to the pubic area of the male participant. The third patent provides an absorbent material, and a wiping/sealing slot, but is not actually sealed. Furthermore, during a sexual activity, the extending member of the male partner may come out and be reinserted in the orifice/slot multiple times, and when doing so, it touches the outer surface of the garment which can both smear it with bodily fluids of the potentially infected female user and also since the outer surface is in continuous contact with the pubic area of the male user, it may be infected by the potentially infected male partner. Thus a male condom touching the potentially infected outer area of the shield and then being slid inside the wearers vagina may transfer the infection from the outer surface of the garment to the body of the female wearer. A solution like the first said patent also may tear the male condom due to friction between the orifice of the latex garment and a latex condom. It is very well known that latex friction tears a male condom. The present invention may be more effective to prevent STD than said patents. There is less risk of tearing a male condom due to use of materials such as silicon and TPE for the orifice those are proven to be safe with latex condoms as they are common material for sex dolls. In some implementation of the present invention there is no penetration. In case of penetration sex activities, multiple solutions are suggested those include double sealing the orifice to reduce bodily fluids leakage from the female side, having a drainage system for the bodily fluids which may have an optionally replaceable absorbent pad. Also various shapes for the orifice entrance is suggested for example a sealing orifice to limit the leakage of bodily fluids, a conic orifice entrance to avoid contact of the pubic area of the male partner with the entrance and to facilitate re-entering the male extending body part without touching the surrounding area which with proper education and practice may reduce the chance of contagiousness. A brief style fly shaped barrier solution is also suggested to safely prevent contact between the pubic area of the male user with the smeared outer surface of the pubic area of the protective wearable device and also allow safe oral sex. Also a special male rubber dam mask is suggested to cover STD prone areas those are not generally covered by a condom. Use of such solutions may reduce the risk of STD to almost zero.

U.S. Pat. No. 5,413,117 also has another disadvantage against the present invention: The absorbent material is in direct contact with the genital of the female user which means it absorbs the bodily fluids and result in a dry penetration after a short period of use. The suggested absorbent material of the present invention is suggested to be in a drainage cavity located after a first seal which means it will only absorb the fluids those pass a first seal and will not result in dryness. Another absorbing solution is suggested for the external surface of a wearable device which may absorb leaked bodily fluids without causing dryness.

U.S. Pat. No. 5,181,527 dated Jan. 26, 1993 by James C. Dorsey provides a wearable pubic area shield with an opening and an expandable sheath acting similar to a female condom. A similar approach is proposed by many patents including U.S. Pat. No. 4,862,901 dated Sep. 5, 1989 by Ivan L. Green, US2005/0087193A1 dated Apr. 28, 2005 by Sylvia Scott.

U.S. Pat. No. 5,535,757 date Jul. 16, 1996 by Fleming Jr. provides an undergarment for a female wearer with an opening at the genital area with attachable female condoms and oral sex specific condoms.

Patent No. US 2013/0160774 A1 dated Jun. 27, 2013 by Robert J. SCHUMAN discloses a male condom with an accompanied skirt to cover the penis surrounding area which can be rolled together with the condom. The present invention provides a rubber dam mask solution with a similar approach with strapping means to strap it around the waist, buttocks, and legs of the user which is more practical to use since the dam will be fixed unlike said skirt, and can be mass produced much easier. Rubber dams have been used in dental applications since 1864. Rubber dam or dental dam is a 6 inch square thin sheet of latex or nitrile. In order to use an oral dam for dental works, a small punch hole is made in the rubber dam and the whole is stretched open around one or more teeth. The size of the hole may be stretch to multiple times of the original punch hole size and can withstand such tension. Dental dams are also suggested for performing oral sex for women.

U.S. Pat. No. 5,083,414 dated Jan. 28, 1992 by Cheng M. Wu has a folding extension for a male condom which is not practical for mass production. U.S. Pat. No. 4,955,392 dated Sep. 11, 1990 by Reuben Sorkin, U.S. Pat. No. 4,794,920 dated Jan. 3, 1989 by David M. Robichaud each provide an accompanying protective extension for a male condom. Patent No. US 2007/0193586 A1 dated Aug. 23, 2007 by Grace Elizabeth Vaughn, provides a male condom with an additional surrounding area shield which has two straps to strap it around the waist of the user. However, A not roll-able condom is not easy to wear.

BRIEF SUMMARY OF THE INVENTION

The present invention discloses wearable prophylactic and intimacy aid devices for couples, being worn by a first user/wearer, to have a sexual activity potentially with at least one second user, said devices may be produced out of material mimicking human flesh, and having outer surfaces mimicking actual human skin and having built in cavities those mimic human body orifices in order to provide new possibilities in a sexual relationship.

The present invention suggests employing the advancements and materials used in sex dolls/robots industry and female sex toys, for producing wearables those actually mimic living body parts of a human, such wearables when worn by a wearer, independently or in combination with parts of the body of the wearer, provide entryways orifices, and cleavages those can be used for penetration.

In addition to one or more of the features described above or below, or as an alternative, further embodiments could include wherein said device can be used to visually enhance the size of body parts of the wearer (e.g. breasts, buttocks, hips, thighs) both when worn under the dress or without a dress.

In addition to one or more of the features described above or below, or as an alternative, further embodiments could include wherein at least one orifice on the apparatus has two open ends and is positioned in line with a body orifice of the wearer in order to allow sexual intercourse. Depending on the size, such orifice may act as a seal to keep the bodily fluids of the wearer inside. Different designs are suggested, including an orifice with a double sealing design, at least one with a drain preferably between the seals, which may have a replaceable absorbent material in the drain. Said at least one orifice may act similar to a circular muscle/sphincter to enhance the pleasure of the male participant.

In addition to one or more of the features described above or below, or as an alternative, further embodiments could include wherein at least one wall of a cavity of the wearable prophylactic and intimacy aid device being a part of the body of the wearer. It may include but not be limited to the wearers clitoris, parts of the chest skin (e.g. between the breasts), nipples, lower back, hip area, thighs and even areas where interest in them is categorized as fetishism including feet and hands.

In addition to one or more of the features described above or below, or as an alternative, further embodiments could include wherein one part or the complete outer surface of said wearable apparatus being clad to look like an actual outfit. The outer cladded may look like a pantie, bra, top, shorts, skirt, etc.

In addition to one or more of the features described above or below, or as an alternative, further embodiments could include wherein said wearable prophylactic and intimacy aid device is used to push two parts of the body of the wearer together (e.g. breasts, two legs, buttocks) in order to create a cleavage to be used for penetration. Said device may have an orifice to guide the means of penetration in said cleavage.

In addition to one or more of the features described above or below, or as an alternative, further embodiments could include wherein a wearable prophylactic and intimacy aid device covers at least one of genital area and anus of a wearer, having at least one entryway in the form of an orifice/slot to allow sexual intercourse with at least one of a vagina and an anus of a wearer, further including a "brief style fly" resembling thin sheet made of a flexible material (e.g. latex) supported at the crotch of said device to make a barrier and prevents the STD prone areas of a second user from touching the area around said orifice which may potentially be smeared by the bodily fluids of said first user/wearer.

In addition to one or more of the features described above or below, or as an alternative, further embodiments could include wherein a wearable prophylactic and intimacy aid device covers at least one of genital area and anus of a wearer, having at least one entryway in the form of an orifice/slot to allow sexual intercourse with at least one of a vagina and an anus of a wearer, having an absorbent means to absorb bodily fluids leaking out of said entryway, said absorbing means including a strip made of a layer of absorbent material covering the outer surface of said device encircling said entryway, configured to have a clearance of at least 1 millimeter with a means of penetration penetrating said entryway, the top surface of said layer of absorbent material being covered by at least one layer of STD resistant material.

In addition to one or more of the features described above or below, or as an alternative, further embodiments could include wherein said wearable device is in the form of a sport bra, supporting the breasts of the first user/wearer, having an orifice/cavity which guides the body extending member of a second user between the breasts of the wearer to facilitate having mammary intercourse. Such device may have breast size enhancing means.

In addition to one or more of the features described above or below, or as an alternative, a special male rubber dam barrier mask is suggested to be worn over a male condom and cover STD prone areas such as pubic area, scrotum, upper thigh an upper groins to enhance protection against STD.

DETAILED DESCRIPTION OF THE INVENTION

Figure 1:
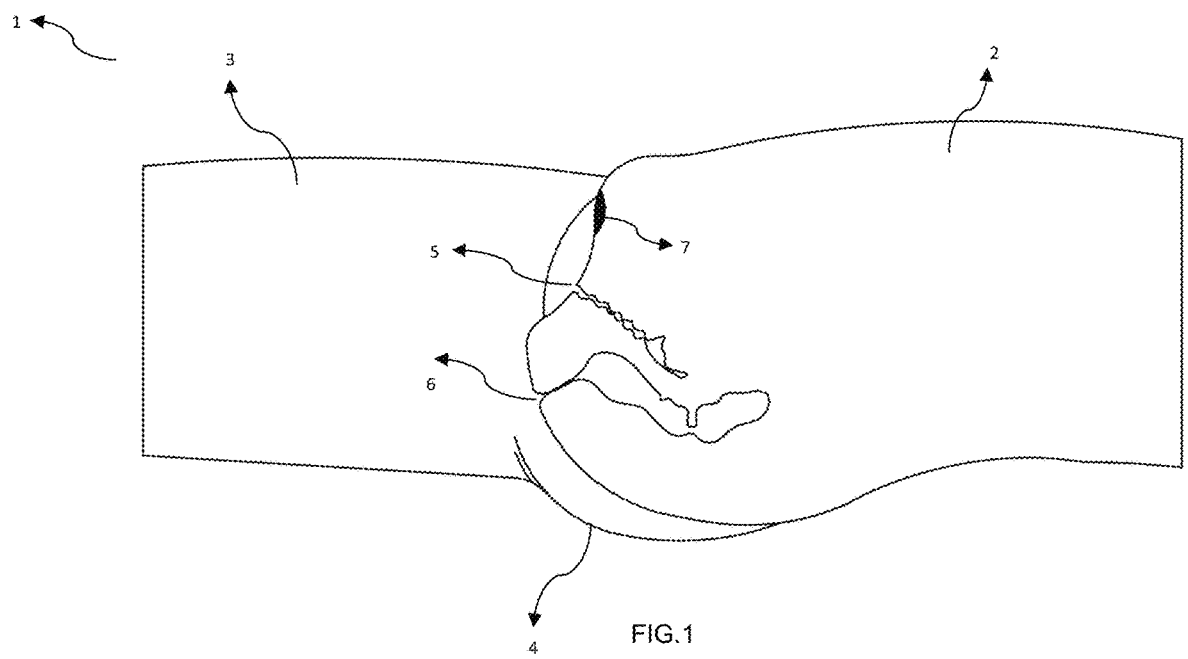
FIG. 1, is a basic female sexual anatomy sketch that the apparatus shown in the next figures will be illustrated around it.

A detailed description of the embodiments of the disclosed invention and methods is presented herein by way of exemplification and not limitation with reference to the Figures.

While the disclosure is provided in detail in connection with only a limited number of embodiments, it should be readily understood that the disclosure is not limited to such disclosed embodiments. Rather, the disclosure can be modified to incorporate any number of variations, alterations, substitutions or equivalent arrangements not heretofore described, but which are commensurate with the spirit and scope of the disclosure. Additionally, while various embodiments of the disclosure have been described, it is to be understood that the exemplary embodiments may include only some of the described exemplary aspects. Accordingly, the disclosure is not to be seen as limited by the foregoing description, but is only limited by the scope of the appended claims.

The terminology used herein is for the purpose of describing particular embodiments only. It is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements and/or components, but do not preclude the presence or addition of one or more other features, integers, steps, operations, element components and/or groups thereof.

The present invention discloses wearable prophylactic and intimacy aid device for couples, being worn by a first user/wearer, to potentially be used for having a sexual activity with a second user, said devices may be produced out of material mimicking human flesh, and having outer surfaces mimicking actual human skin and independently or in combination of with the body of the wearer, provide entryways to be used for a sexual penetration.

There may be occasions when a person has the intention to get engaged in a sexual relationship with a male partner but for personal, religious, medical, hygiene reasons, or physical reasons or limitations does not have the intention or the possibility to have at least one kind of sexual activity such as a sexual intercourse, oral sex, anal sex, mammary intercourse, intercrural sex, etc. with said partner. Said reasons, conditions or limitations may include but not be limited to menstruation, virginity, medical conditions, pregnancy, post-surgery, after or during cancer treatments, injury, size and shape of body parts (e.g. breast), being in the early stages of a relationship, personal dislikes, beliefs or preferences, gender, etc. The present invention may be a relationship saver in such situations by providing a natural feeling solution to mimic such sexual activities.

The sex dolls and sex robots industry has been evolving rapidly in the recent years. The sex robots and sex dolls now seem much more attractive and realistic both for the eye and the body of the person who uses them. However, they are still not real. The present invention has the intention to employ the advancements of manufacturing sex dolls/robots, for using wearables those actually mimic living body parts of the user and using such wearables independently or in combination with actual body parts of the wearer.

Wearing butt pads, silicon padded underwear, hip enhancer pads, padded bras and similar products to shape buttocks, hip, legs, and breasts is very common for cosmetic reasons. While such products are mainly worn under the dress of the wearer, the present invention suggests making similarly shaped wearable pieces made of materials mimicking human flesh and skin such as the ones used in sex doll industry both under the dress and during a sexual relationship. Such products may have cavities, orifices, cleavages, grooves, valleys, depressions, etc. those independently or in combination with wearers' body parts may simulate cleavages or orifices such as anus, vagina, mouth, throat, and help to simulate sexual activities such as but not limited to sexual intercourse, mammary intercourse, intergluteal sex, intercrural sex, axillary intercourse, hand job, foot job, etc.

Common materials used for sex dolls are Silicone and Thermoplastic elastomer (TPE). Frubber (Flesh rubber) is a patented material use by Hanson Robotics. Advance elastomeric gels are also considered a new material in this field. There are also various trade names such as Cyberskin, Softskin, or UltraskinSilicone. Silicone is considered a safe material due to its non-porous nature. Some areas of the present invention need to provide protection. When a thin layer is required, Latex is considered the first choice for protection. However, latex parts cannot be used together with a latex condom since the condom may tear due to friction. Polyisoprene and polyurethane are considered replacements for commercial latex. Hydrogel is a "slippery, soft" material being developed for use in condoms. Medalist® TPE by Teknor Apex Company is intended to replace latex in many different applications. The present invention is not limited by the materials. Flesh and skin mimicking materials are common knowledge in this industry and will be referred as "Flesh mimicking materials" and "Skin mimicking materials". Flesh mimicking materials are required for making bodies and for some areas, protection layers and barriers may be suggested those may be produced out of every common material used in sex dolls, sex robots, sex toys and condom industries.

Figure 2:
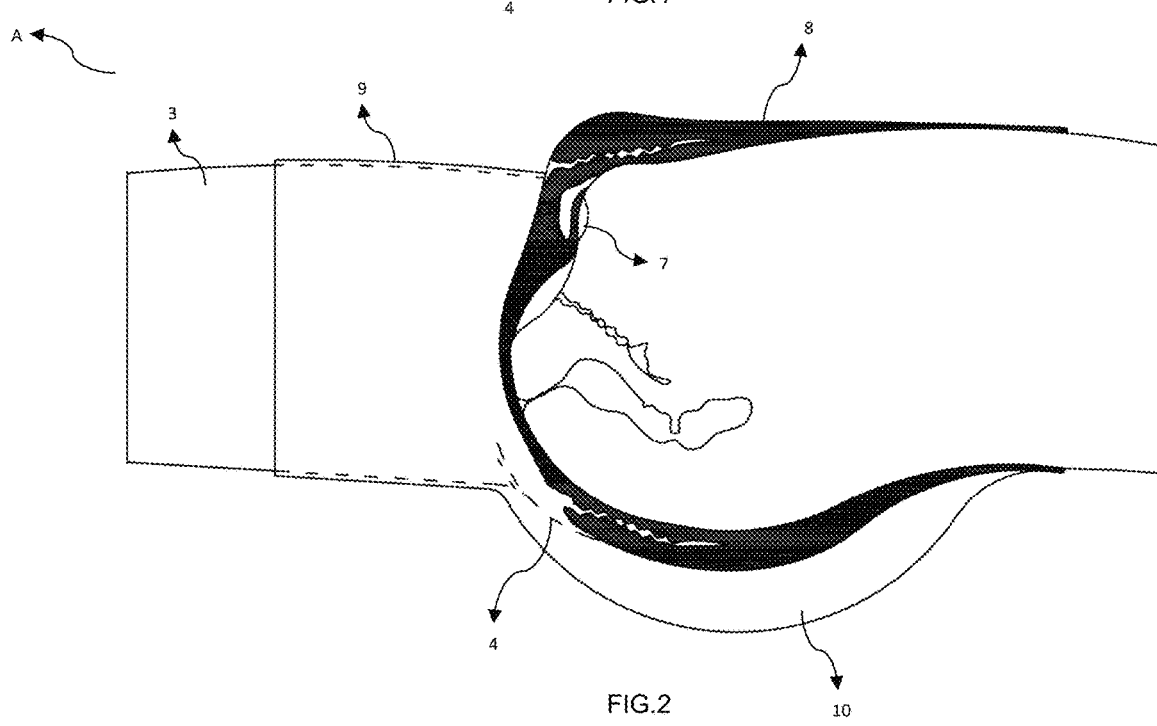
FIG. 2, shows a section view of embodiment A of the present invention worn by a female wearer.
Figure 3:
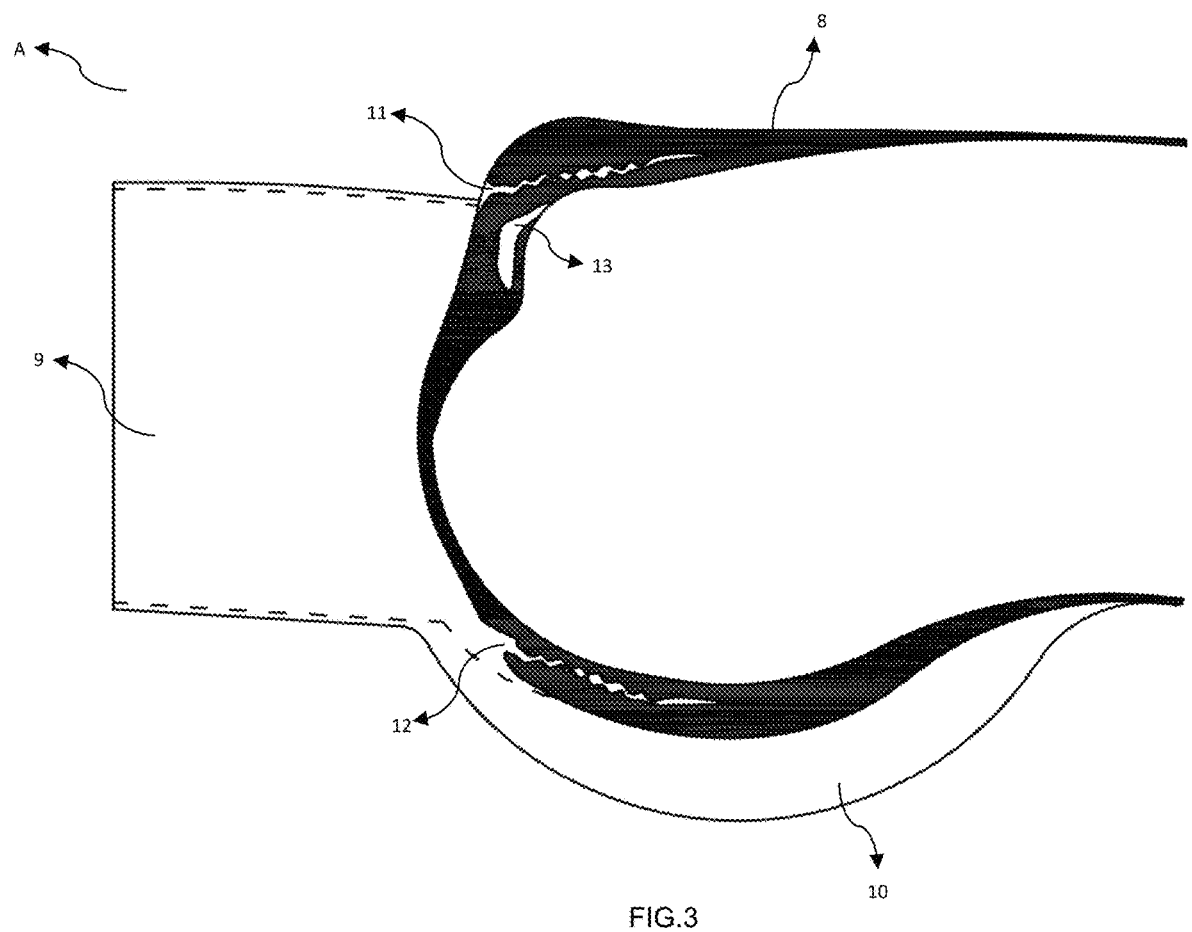
FIG. 3, shows a section view of embodiment A of the present invention.

FIG. 1, is a basic female sexual anatomy sketch of the body of the wearer 1, a female user that the embodiments shown in the next figures will be illustrated around it. The wearer is also referred as first user of the device in this document. The figure also shows the wearers abdomen 2, leg 3, buttocks 4, Vagina 5, Anus 6, Clitoris 7. FIG. 2, shows a section view of embodiment A of the present invention worn by a female wearer 1. The wearable device 8 has legs 9 that cover wearers legs, a body 10 to enhance the size of the buttocks 4 and hips of the wearer. FIG. 3, shows a section view of embodiment A. A cavity mimicking vagina 11 and a cavity mimicking anus 12 on the back of the device are shown. An optional vibrator engine cavity 13 is also displayed for stimulation of the clitoris 7 of the wearer 1. Said vibrator also vibrates the vagina mimicking cavity 11 as an additional means of stimulation for the second user. A vibrator may be a fixed device inside the faux flesh, or a replaceable insert.

Figure 4:
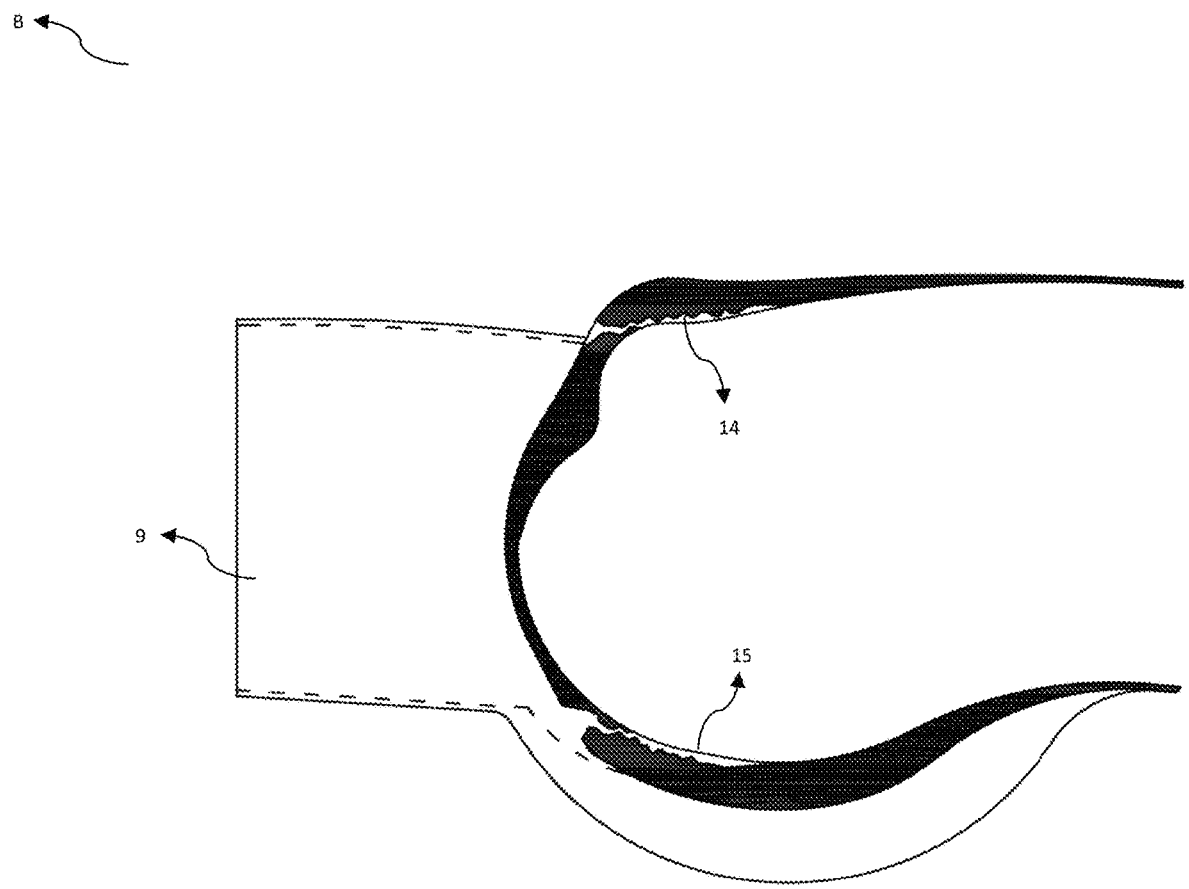
FIG. 4, shows a section view of embodiment B of the present invention.

If protection is not an issue for users, a cavity may be adjacent to the body of the wearer, and have an open wall to allow contact between the skin of the second user and the wearer. FIG. 4 shows such concept as embodiment B. A skin adjacent cavity 14 mimicking a vagina and a skin adjacent cavity 15 mimicking an anus are displayed. However, the cavity 15, technically may enable stimulation of the penis of a second user with the buttocks of the wearer which is called Interglueal sex and classifies as non-penetrative sex. If protection is a concern, the second user may wear a male condom. As an alternative, a protective underwear may be worn under the embodiment B by the first user. For example an underwear which is partially or totally made of latex. Also replaceable sheets or similar protective material may be devised to be connected inside the device 8.

Figure 5:
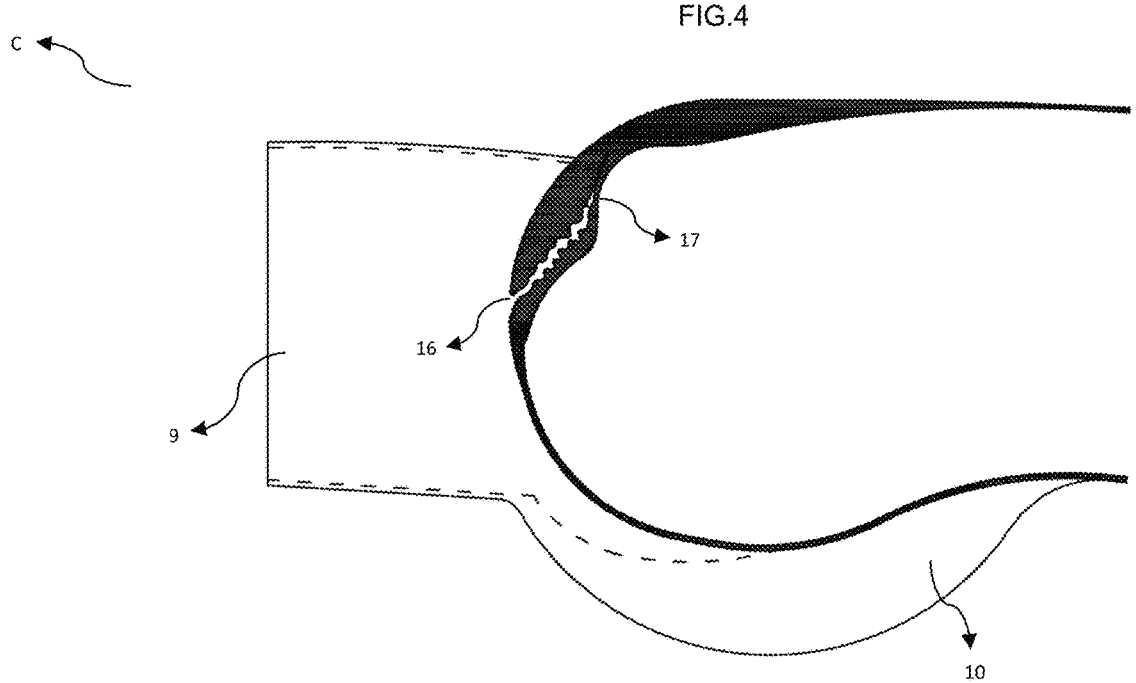
FIG. 5, shows a section view of embodiment C of the present invention.

FIG. 5 shows another implementation of the device as embodiment C. A cavity 16 is devised to pass close to the clitoris of the wearer 1 to create stimulation of clitoris when used. The cavity 16 side walls may have reduced thickness or be fully eliminated in order to allow intercrural sex from behind. The intercrural sex using this device may be more pleasurable than the natural way due to the additional grip of the cavity and orifice opening. The cavity 16 may have another opening in the front to allow intercrural sex from the front too. A modified embodiment can be proposed with one leg opening instead of two, allowing one opening of the device to embrace both legs and push them together for a better intercrural sex experience. The thin separating layer 17 separates the second users extending member from the clitoris 7 of the wearer 1. The thin separator 17 may be eliminated similar to embodiment B by considering the same protection measures in order to provide more stimulation of the clitoris.

Figure 6:
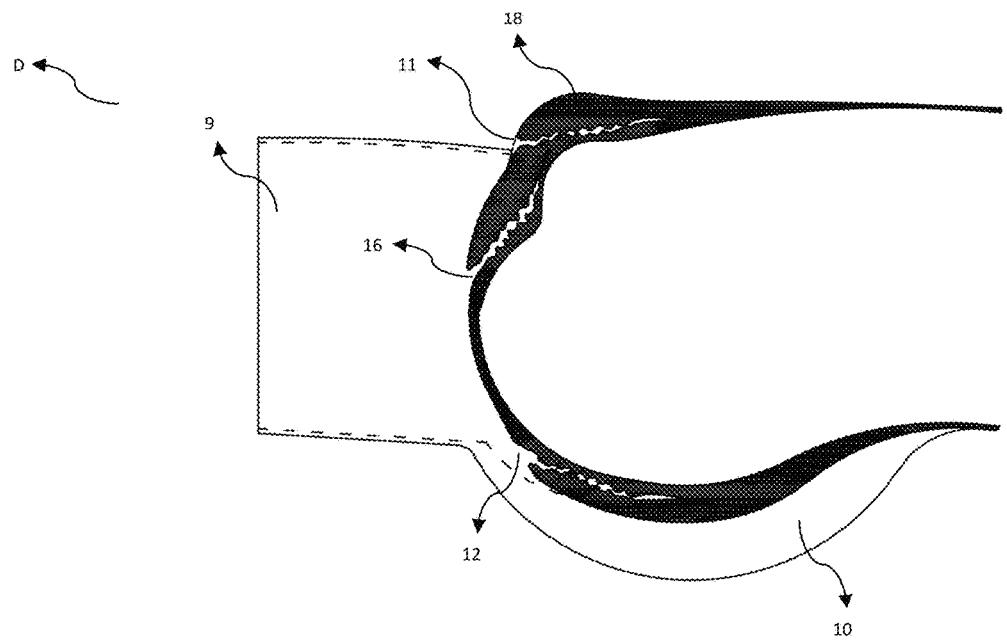
FIG. 6, shows a section view of embodiment D of the present invention.

FIG. 6 shows Embodiment D of the present invention. This embodiment has both cavities 11 and 12 together with cavity 16. So there will be totally three cavities. Thus theoretically, the present invention may provide more orifices than the natural body of the wearer. The protrusion 18 mimics the pubic bone protrusion.

Figure 7:
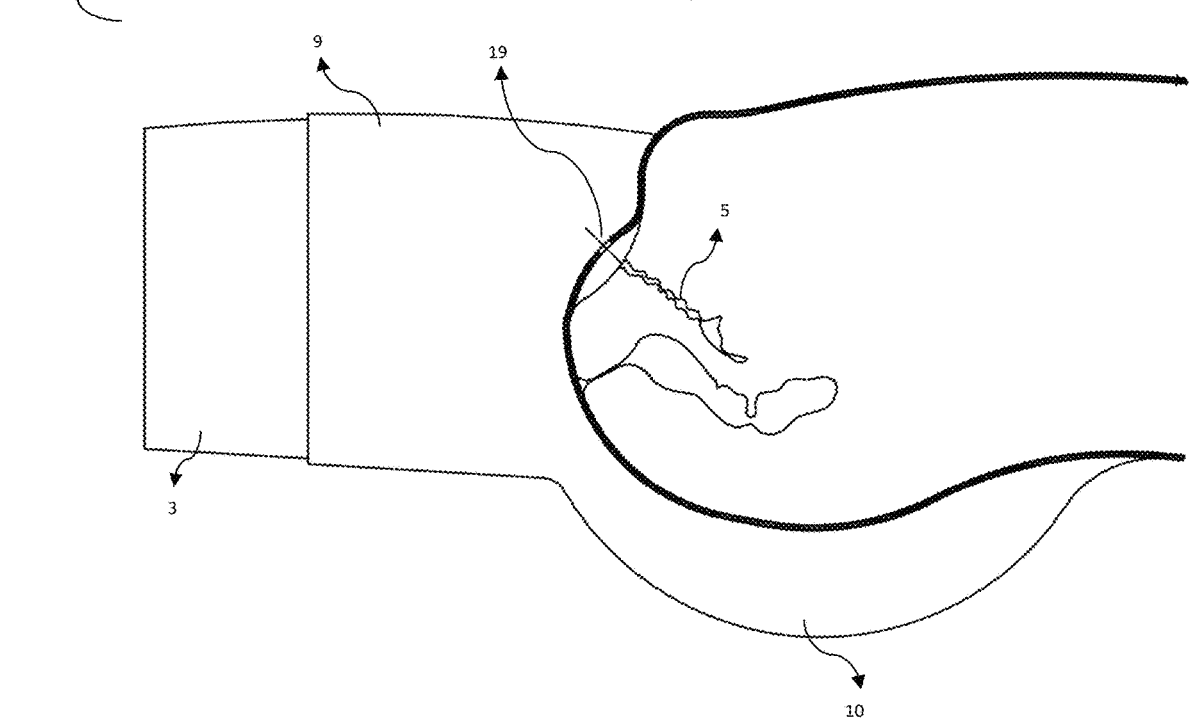
FIG. 7, shows a section view of embodiment E of the present invention.
Figure 8:
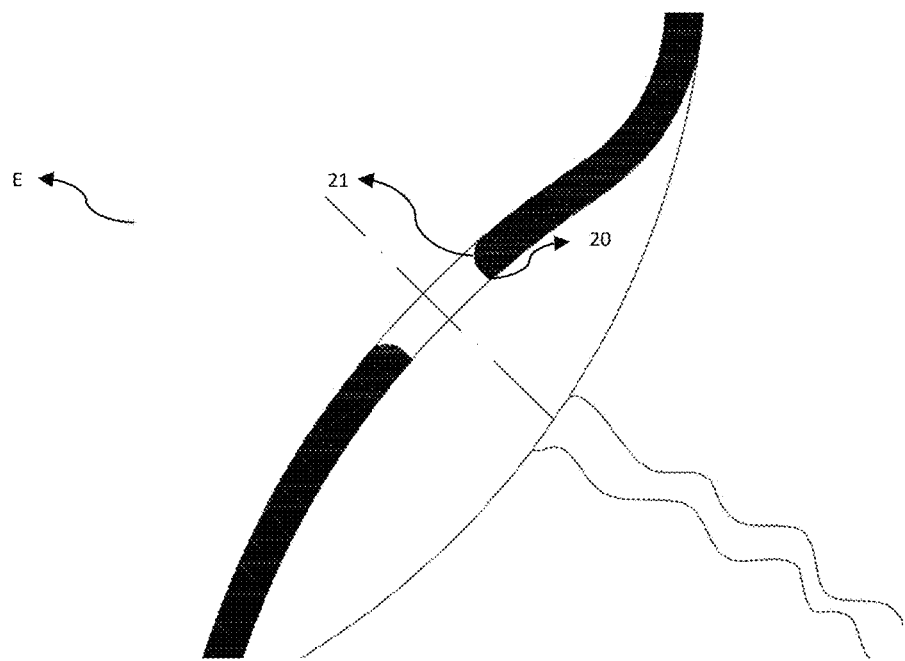
FIG. 8, shows a section view of sealing orifice of embodiment E of the present invention.
Figure 9:
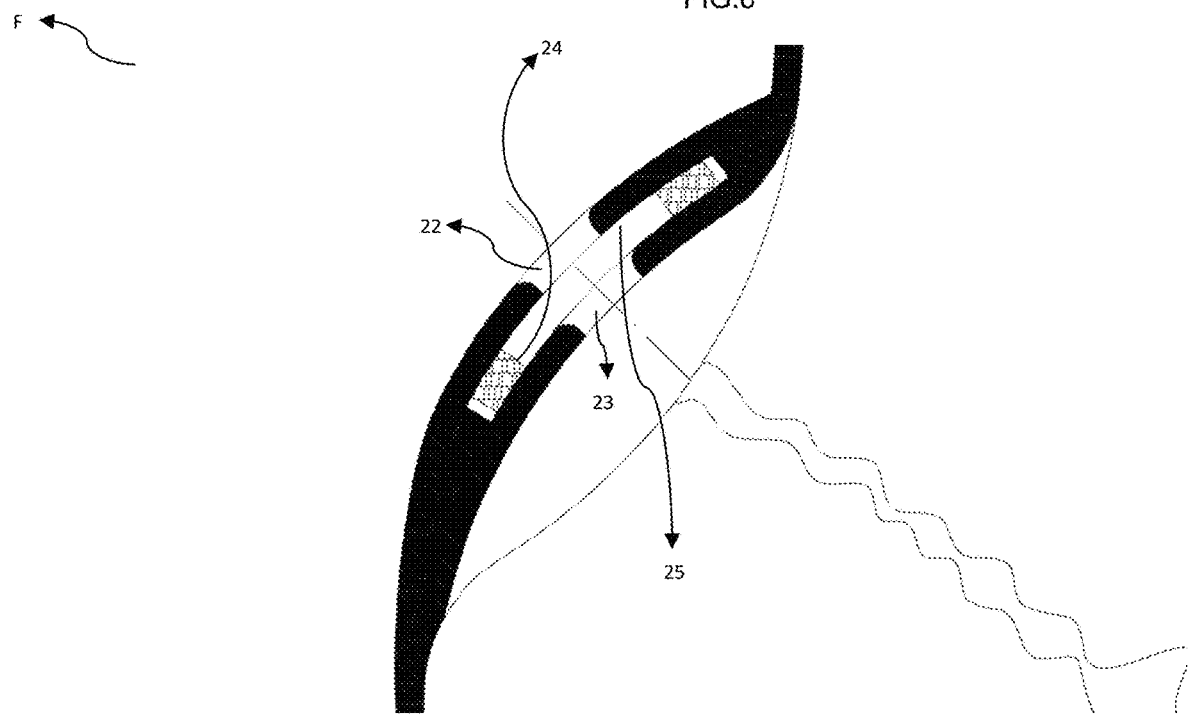
FIG. 9, shows a section view of double sealing orifice of embodiment F of the present invention.

FIG. 7 shows Embodiment E of the present invention. It's basically made of a thin layer of material and does not have any cavities. However, a tight orifice which is aligned with the vagina 5 of the wearer acts similar to a circular muscle/sphincter and provides additional grip to the penis 27 of the second user resulting in increased pleasure. Also the device if used together with a male condom, eliminates skin to skin contact which means better protection against STD. There may be double sealing both to enhance protection and pleasure. This figure displays a sealing orifice 19 which is aligned with the users vagina 5. FIG. 8 shows a close up view of the same orifice. An inner side of the orifice is shown to have a sharper edge while the outer edge has a more rounded shape. The rounder shape allows liquids attached to the body extending member of the user going inside the orifice easier (e.g. lubricant) while the sharper edges has the tendency to wipe liquids off (e.g. bodily fluids of the first user). FIG. 9 shows a double sealing orifice concept as a part of embodiment F. It includes an outer orifice 22, and an inner orifice 23, each having a sharper edge on the inside and a more rounded edge on the outside. The sharper edge wipes the bodily fluids off the body extending member of the second user. However, a soft material should be chosen for the orifices in order to offer better sealing and also avoiding excess friction with a condom to avoid tearing it. A cavity/groove 25 is displayed between said orifices. This area acts as a trap for the bodily fluids that escape the inner orifice 23. It is possible to devise a draining tube/a hole from the trap cavity 25 to drain the bodily fluids. However, such hole may be tricky to clean. As an alternative, an optional replaceable absorbent material 24 is also displayed which may have a round shape to fit inside the trap cavity 25 between said orifices. It has a larger diameter than the body extending member of the user, thus it will not wipe the body extending member of the second user. Only the excess trapped bodily fluids will be absorbed and the absorbent material will not cause a dry intercourse. While the rounded outer edges of the orifices have less wiping effect, they still do wiping, thus it is suggested to inject lubricants inside the vagina 5 instead of applying it on the body extending member of the second user. The groove shaped cavity 25, may also be used as a seat for the lip of a female condom, so that a female condom being fixed in the groove 25 to be used during a sexual intercourse.

Figure 10:
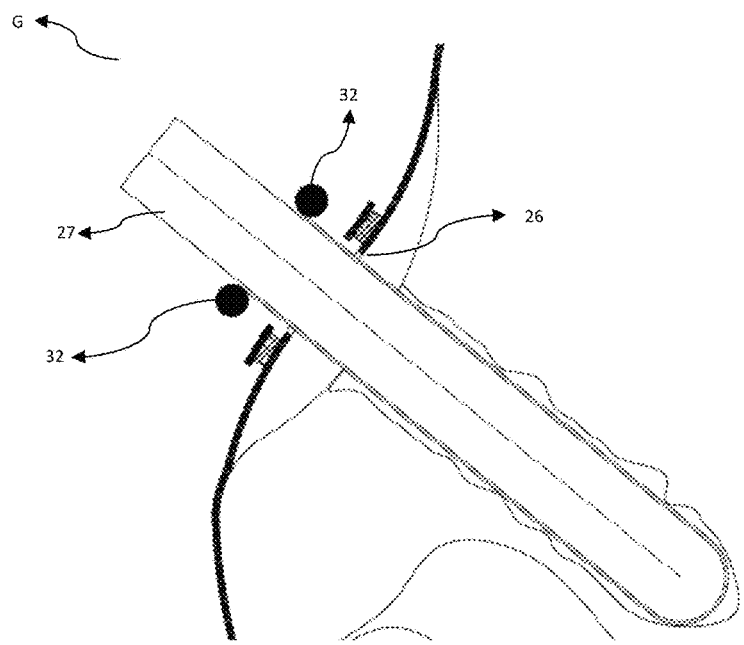
FIG. 10, shows fluid absorption solution for embodiment G of the present invention.
Figures 11, 12:
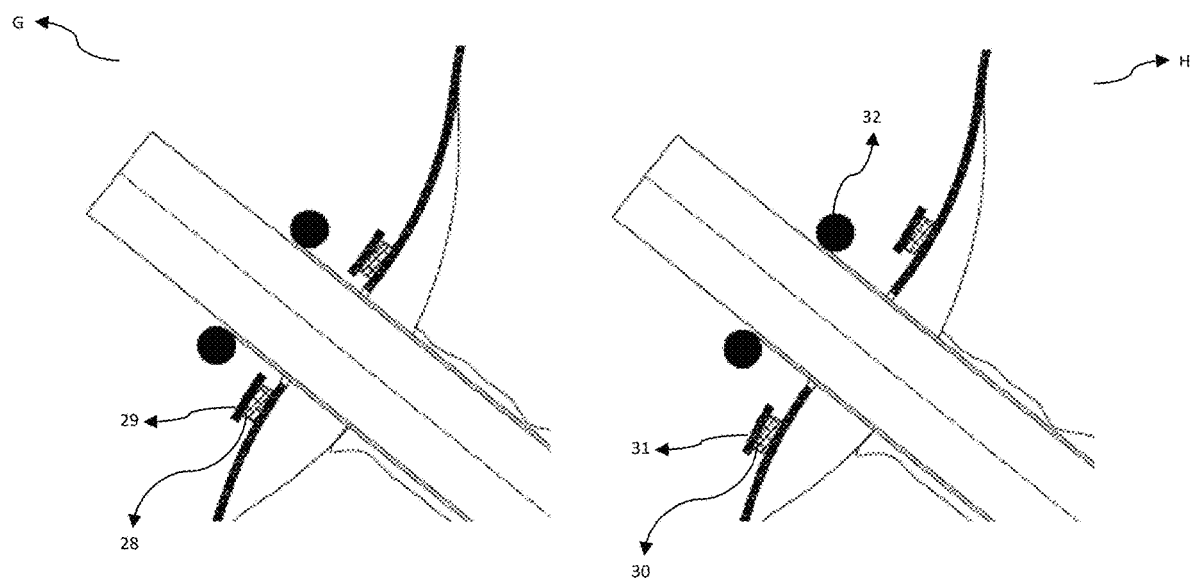
FIG. 11, shows fluid absorption solution for embodiment G of the present invention.
FIG. 12, shows fluid absorption solution for embodiment H of the present invention.

A absorbent material may also be used on the outer surface of an opening. FIG. 10 and FIG. 11 show such concept as embodiment G. The opening 26 showed in the images is bigger than the size of a penis 27. Thus it will not have wiping effect on the penis 27 or condom 32. A strip made of layer of an absorbent material 28 has encircled the opening 26. Another layer of STD resistant material (e.g. latex) 29 has covered the external surface of the absorbent material to avoid contagiousness of STD through the absorbent material. FIG. 12 shows embodiment H which is the same as embodiment G and the only difference is that the diameter of the absorbent material 30 and protective layer 31 is bigger, thus having more clearance with the penis 27 and condom 32.

Figure 13:
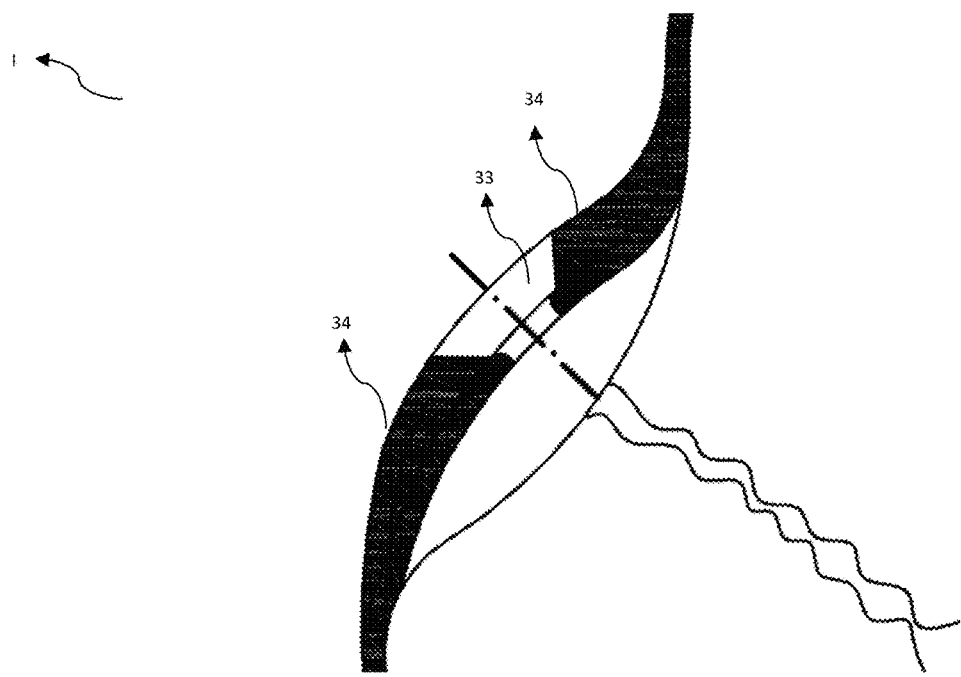
FIG. 13, shows a section view of conic sealing orifice of embodiment I of the present invention.

FIG. 13 shows the concept of having a conic orifice 33 as a part of Embodiment I. The intention of having a conic surface is facilitating the reinsertion of the body extending member of the second user in case it comes out during a sexual intercourse. Having a conic orifice 33, means reinsertion will most probably smear the conic area than the surrounding area 34. The pubic area of the second user will contact the surrounding area 34, and cannot touch the conic area 33. With a little practice, the second user may be able to avoid smearing the surrounding area 34. Thus a conic design can reduce the risk of STD by reducing the contact between a smeared area and the pubic area of the second user, while not 100% eliminating the risk.

Figure 14:
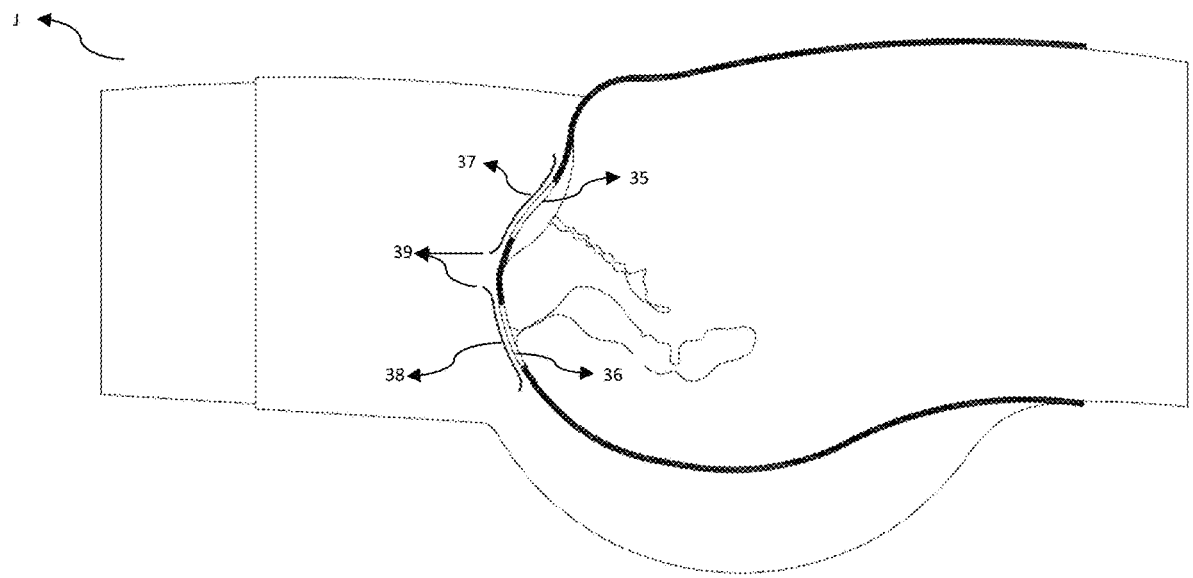
FIG. 14, shows embodiment J, a brief style protective fly for a protective garment opening with curved free ends.
Figure 15:
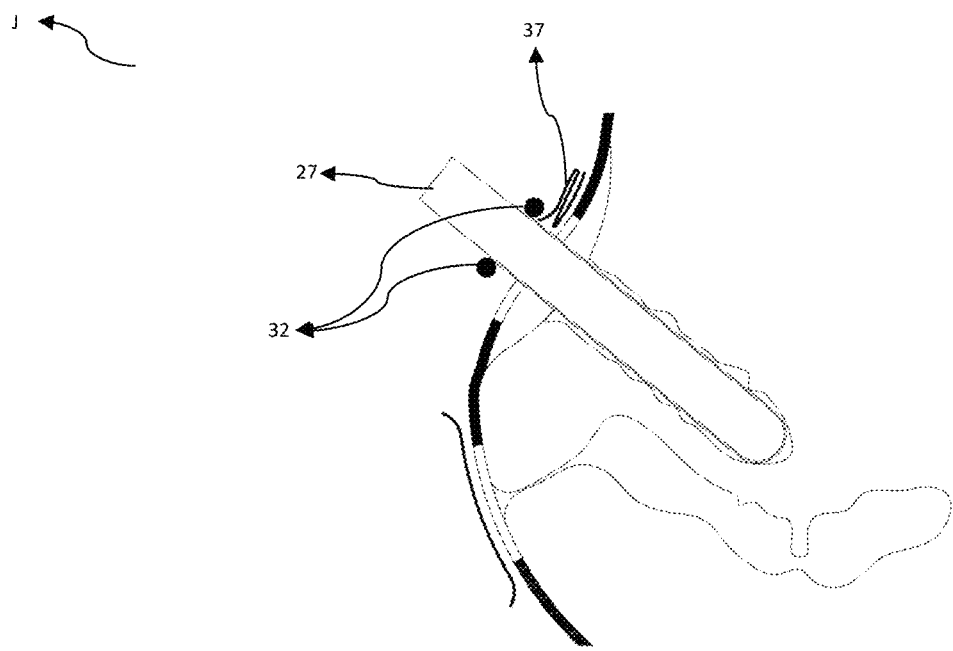
FIG. 15, shows a section view of embodiment J, a brief style protective fly for a protective wearable, being stretched to allow penetration.
Figure 16:
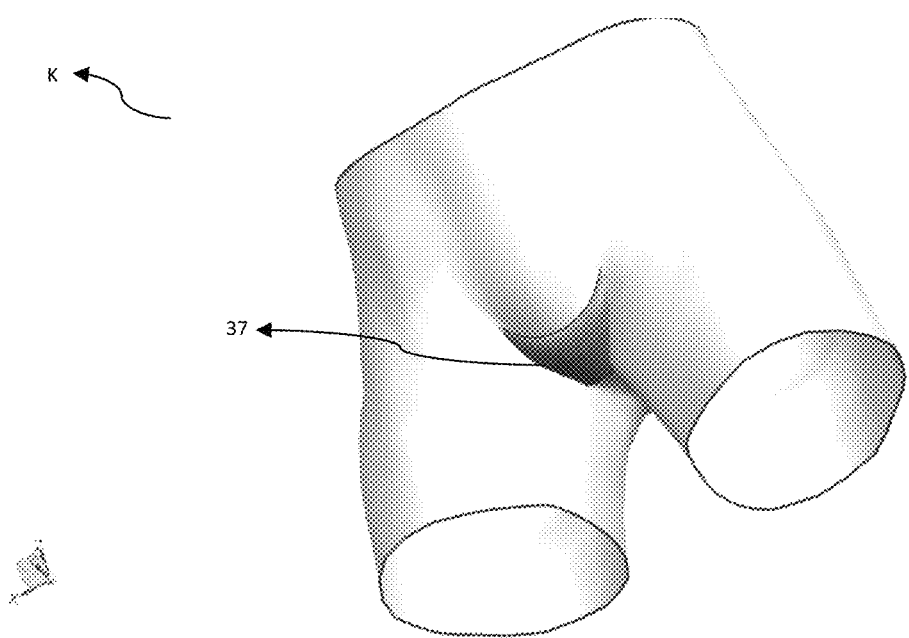
FIG. 16, shows a 3d view of embodiment K, having a brief style protective fly for a protective wearable opening.

FIG. 14 shows brief style fly protection layer concept as embodiment J. The displayed embodiment has two slot shaped openings 35 and 36 and two brief style fly protection barriers 37 and 38. Each fly barrier is fixed at two ends to the right and left sides of the opening, to the crotch or upper groin areas. As it can be seen, the edges 39 may be curved. FIG. 15 shows embodiment J during penetration. Curved edges 39 can be helpful since a finger can be slid below the fly type barriers without using nails those can tear the device. Another brief style fly barrier 38 is displayed for the anus. FIG. 16 shows a 3d image of embodiment K having a brief style fly barrier 37. A brief style fly barrier may also be practical for performing oral sex for a female wearer.

Figure 17:
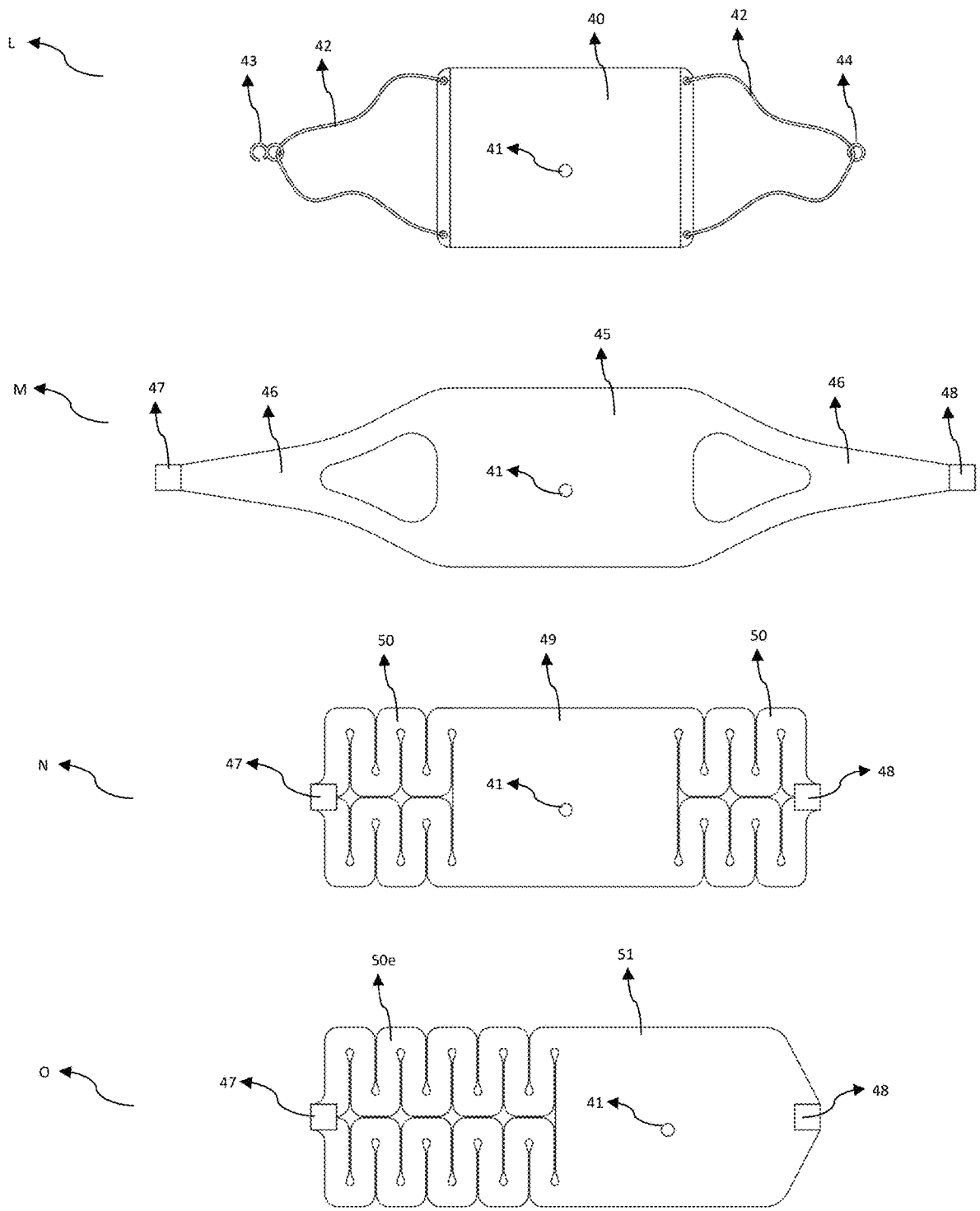
FIG. 17, shows embodiments L, M, N, O of male rubber dam mask.

The presented embodiments can each reduce the risk of STD in a way. Novelties described on embodiments E to K can be combined by other embodiments. For example, embodiment A may be configured to have an additional orifice similar to a vagina opening orifice 19. It is also possible to provide disclosed orifice types, seals, absorbent solutions, and brief style fly barrier disclosed as part of embodiments E to K on a simple prophylactic device made in the form of a latex underwear having at least one opening for penetration, designed to be used together with a male condom. Addition of the presented novelties to a latex underwear will reduce the risk of STD by reducing the probability of contact between STD prone areas of a male user with potentially smeared areas around an opening of said prophylactic Device. For such device, use of a brief style fly will also provide the possibility of performing a safe oral sex. However, another means of protection is begin disclosed which in combination with the presented novelties, can reduce the risk of STD to almost zero. Rubber dams have long been used in dental applications. Rubber dam or dental dam is a 6 inch square thin sheet of latex or nitrile. In order to use an oral dam for dental works, a small punch hole is made in the rubber sheet and the hole is stretched open around one or more teeth. The size of the hole may be stretch to multiple times of the punch hole size and can withstand such tension. Dental dams are also suggested for performing oral sex for women. The presented solution acts similar to the dental use of a rubber dam. It includes a sheet of thin flexible STD resistant material, such as Latex similar to a dental dam. A punch hole is made in said sheet at a diameter of about 10 millimeters. It can be safely stretched to diameters such as 30 or 40 millimeters. The device maybe worn both before and after wearing a condom. But wearing it after wearing a condom is much safer because the stretched punch hole position will be fixed by said condom's rim. Size of said barrier should preferably big enough to mask HPV and wart prone areas such as pubic area, scrotum, groins and even upper thigh. Right and left sides of said barrier need to be connected to a strapping means and the whole assembly is stretched and strapped around the body of the wearer. FIG. 17 shows four different embodiments of said device. Embodiment L has a flexible barrier 40, having a hole 41 for a penis 27, two strapping means 42, and a hook and eye fastening means 43 and 44. Every type of strapping means may be used and the presented novelty is not limited by such means. Also every type of fastening means may be used such as but not exclusive to clasps, snaps, studs, buttons, tie, hook and eye, toggles. The fastening means may be on the back of a wearer similar to a bra, on one side or on the front at one side of the mask. The disclosed novelty may not be limited by the type and position of the fastening means. Embodiment M has a main barrier 45 a hole 41, two strapping means 46, and means of fastening 47 and 48. This embodiment is differentiated from the previous embodiment since the straps are integral with the main barrier. The same approach is used for embodiment N, but all the lines are cut from one single rectangular sheet to limit use of raw material and optimize the package size. Embodiment N includes a main barrier 49, stretchable strapping means 50, and fastening means 47 and 48. Embodiment O has a main barrier 51, a hole 41, strapping means 50e, and fastening means 47 and 48. In case of embodiments N and O, some of the lines may not be fully cut and instead be partially perforated to be separated upon pulling the fastening means by the user in order to make handling and packaging easier. Since the material is highly stretchable, the length of straps may be made much shorter than the perimeter of the body of the wearer, to be stretched upon wearing.

Figure 18:
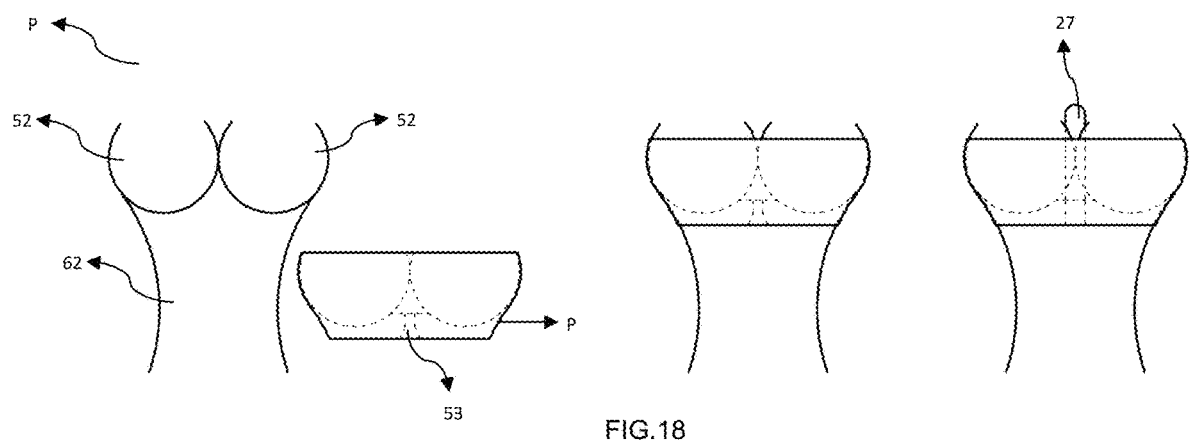
FIG. 18, shows a sport bra style intimacy aid device as embodiments P.
Figure 19:
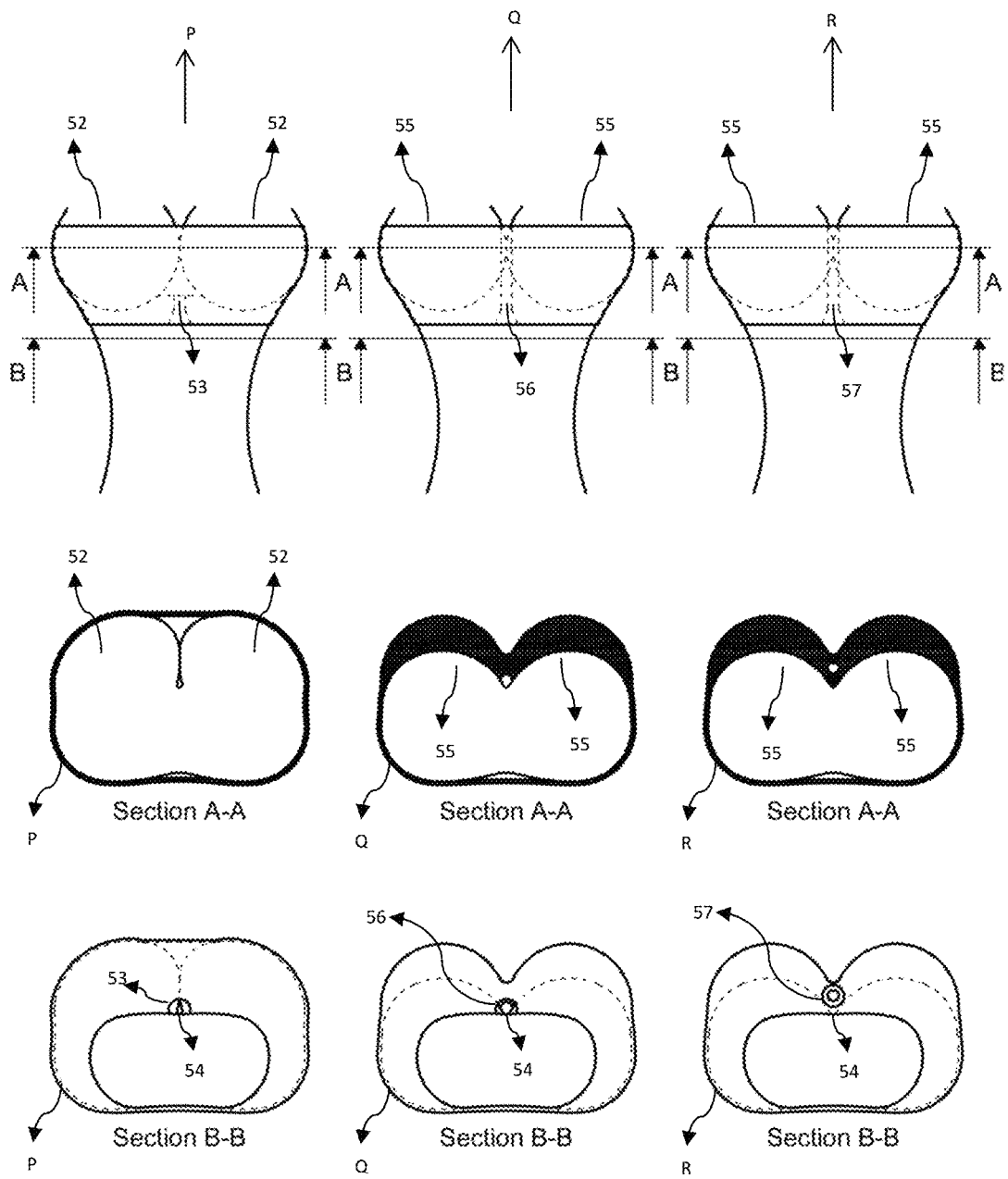
FIG. 19, shows embodiments P, Q and R, in the form of sport bra style intimacy aid devices.

FIG. 18 shows embodiment P of the present invention. This embodiment is in the form of a sport bra and intended to facilitate mammary intercourse. A user's Torso 62 is displayed including the users breasts 52. Embodiment P has an open end cavity 53 to guide a penis 27. FIG. 19 shows embodiments P, Q and R with more details. Embodiment P is more intended for a wearer with biggest breasts 52. It may be designed in a way to push the breasts 51 of the user toward each other as illustrated. Three sides of the simulated orifice are provided by the cavity 53 and one wall of the orifice is the wearers chest 54. The length of the open end cavity 53 is very short and the penis 27 will be embraced by the breasts 52 and the chest 54 after passing the length of the cavity. Embodiments Q and R are intended for wearers with smaller breasts 55 and have size enhancing bodies preferably made of silicone or TPE. In case of embodiment Q the cavity 56 has an open wall to allow the penis 27 to touch the wearers chest 54. However, the length of the cavity 56 is much longer than embodiment P and may go up all the way along the device height. Embodiment R has a cavity 57 fully devised in the size enhancing body, similar to an orifice of a sex doll. Thus the penis 27 will not touch the chest of the wearer 54. In case of the embodiments P and Q, a male condom is required if protection is a concern. Embodiment R provides full protection on the sport bra covered area.

Figure 20:
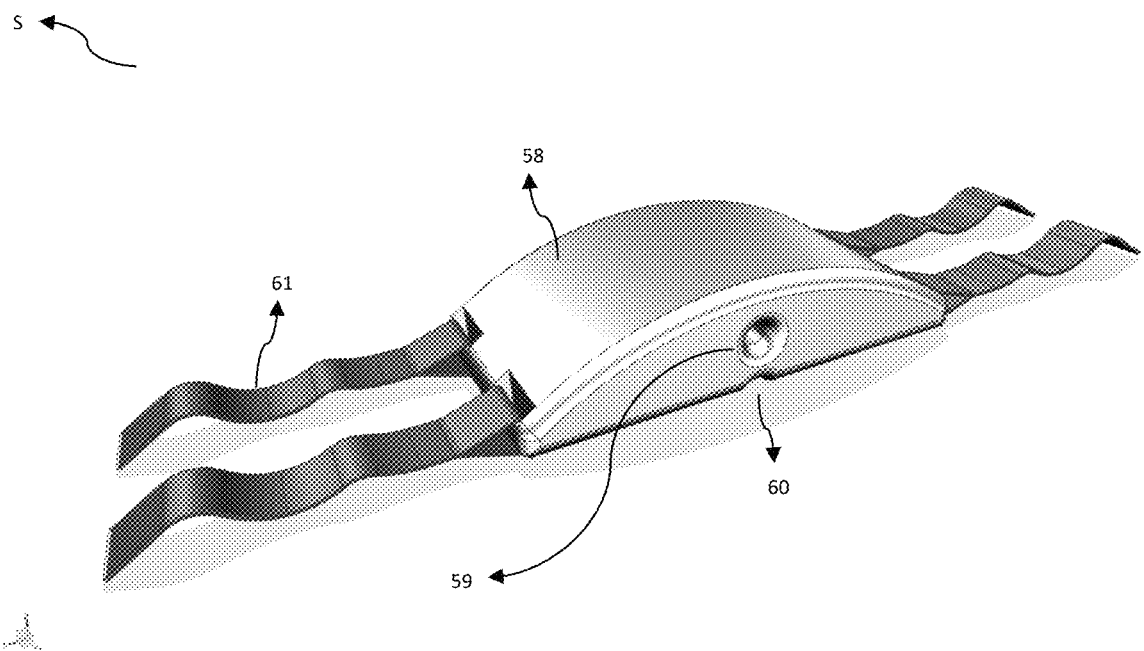
FIG. 20, shows a perspective view of embodiments S of the present invention.

While the application of the present invention is described for mammary intercourse, intergluteal sex, intercrural sex, axillary intercourse, it is to be understood that the present invention can potentially provide unlimited number of embodiments to create an orifice at every part of the body of the wearer and this fact is considered in the claims too. However, a modular embodiment is also provided as embodiment S which is displayed in FIG. 20. Embodiment S includes a flesh mimicking body 58, one orifice 59 which may have a closed or open end, one groove at one side 60 which in combination with a body part of the wearer may create an orifice, and fastening means 61. The body 58 is flexible and can be curved and wrapped around every part and limb of the wearer.

Different designs for mimicking human body orifices such as vagina, anus, mouth, throat has been made and evolved in decades in the sex dolls and sex toys industries. Many industry specific orifices are designed to mimic the feel of vagina, anus, mouth and throat for sex dolls, sex toys and masturbators. They have different internal profiles and patterns. For example there are orifices designed to mimic a throat and they are configured to create a suction effect during a reciprocating penetration. Thus no design has been suggested here for such orifices. Such orifices are considered industry common knowledge and even in the claims section such orifices have only been referred as industry special orifices those mimic vagina, anus, mouth and throat.

Performing penetration by a means of penetration (e.g. a penis, sex toy, finger, tongue, etc.) may provide pleasure both for the first user; the wearer, or the second user, and the act of penetration may be performed by the wearer, or by at least one secondary user.

A cleaning solution may also be suggested for the present invention which includes putting expanders in the orifices of the device and putting the device in a washing machine. The expanders may be in the form of a cylindrical mesh, similar to hair rollers.

Presented embodiments may also become equipped with a lining layer on the inside to reduce sweating. It is also possible to add a skin breathing layer on the inside made of a porous flexible material to allow air circulation around the skin of the wearer. The embodiments may be made in half bodies to be strapped to the body of the wearer by strapping means. For example the sport bra embodiment P may be modified to only have the front half having straps to fasten it. Strapping means may have made of different materials such as fabric, leather, plastic, steel, wood, etc. It is possible to have a textured inner surface for example for the areas those are in contact with a female wearers genital. An outer surface may also be textured for example to improve a sexual activity involving a female second participant. In case of the surfaces those are in contact with latex condoms, for example orifices or the brief style fly, friction is detrimental since it may tear the condom. If the fly is made of latex, it may tear a latex condom. Then it is suggested to add a layer or a coating of a material which causes less friction with latex (e.g. TPE) to said surface. It is possible to add a lubricant storing cavity close to one of the cavities such as cavities 11, 12, 16. Having such cavity inside the pubic bone protrusion body 18 may be a good trick, since the forces applied by the pubic bone of a male sex partner to said protrusion 18 may pump the lubricant for example inside the cavity 11. A lubricant pump may also be devised for pumping lubricant. Each of the cavities and orifices may be replaceable similar to common sex doll orifices, to allow better wash-ability and repair-ability. Said device may also be equipped with a fixed vibrator, a heater or sensors such as tracking sensors, acceleration sensors, temperature sensors etc. Adding a means to create suction for a cavity such as cavities 11, 12, 16 may also be attractive for some users. While the insert cavity 13 is described for an insert-able vibrator, it may be used for variety of other equipment such as a heater, a sensor, etc.

The invention claimed is:

1. A wearable prophylactic and intimacy aid device configured to be worn by a first user, during a sexual activity with a second user including:
    a flexible body of faux flesh made of a flexible material mimicking living human flesh at least in feel and flexibility;
    said flexible body of faux flesh being configured to embrace at least one part of the body of the wearer and acting as an expansion to the body of the wearer;
    at least one receiving entryway to be used for a sexual activity configured to receive at least in part a means of penetration including at least one of a penis, a sex toy, a vibrator, a tongue, a finger;
    said entryway being formed at least one of:
        completely inside said flexible body of faux flesh;
        at least in part between said flexible body of faux flesh and a part of the body of the wearer;
        at least in part between at least two body parts of the wearer;
        at least in part inside said flexible body of faux flesh, having an open end.

2. Wearable prophylactic and intimacy aid device according to claim 1 configured to enhance at least one of the shape, size, style of a body part of the wearer by the means of at least one of its shape, dimensions, and forces applied to the body of the wearer by said wearable device.

3. Wearable prophylactic and intimacy aid device according to claim 1 wherein said receiving entryway is formed at least in part between said flexible body of faux flesh and a part of the body of the wearer including at least one area on the buttocks, belly, chest, lower back, breasts, clitoris, nipples, hands, feet, arms, in order to facilitate a non-penetrative sex activity including mammary intercourse, intergluteal sex, intercrural sex, axillary intercourse, hand job, foot job.

4. Wearable prophylactic and intimacy aid device according to claim 1 wherein said receiving entryway is formed by at least two body parts of the wearer including breasts, legs, buttock halves, arm and torso, calves, feet, hands being one of kept adjacent to each other or pushed together by the forces applied to the body of the wearer by said wearable device, in order to facilitate a non-penetrative sex activity including mammary intercourse, intergluteal sex, intercrural sex, axillary intercourse, hand job, foot job.

5. Wearable prophylactic and intimacy aid device according to claim 1 wherein said at least one receiving entryway at least in part is in the form of an orifice, a cavity, a slit, a slot, a cleavage, an orifice with a conic entrance, and an industry-specific special orifice evolved in at least one of sex-dolls, sex-toys, sex robots industries including an orifice mimicking at least one of a vagina, an anus, a mouth and a throat.

6. The wearable prophylactic and intimacy aid device according to claim 1 wherein the exterior of said flexible body of faux flesh is clad with a material mimicking human skin.

7. The wearable device according to claim 1 wherein the exterior of the device is clad with at least one of "a piece of dress" and "a material mimicking a piece of dress".

8. The wearable device according to claim 1 being at least in part made of an impermeable material resistant to transmission of sexually transmitted diseases.

9. Wearable device in accordance to claim 1 further including at least one of a lining layer on the inside; a breathing layer on the inside made of a porous flexible material to allow air circulation around the skin of the wearer; a strapping means; a textured inner surface; a textured outer surface; a surface one of covered and coated by a material characterized by having low friction with latex to avoid tearing a condom, including TPE; a cavity to store lubricant; a pumping means for pumping stored lubricant to at least one cavity of the device; a replaceable cavity; a replaceable orifice; a built-in vibrator; a built in heater; a sensor; a part not made of a human body mimicking material including fabric, steel, wood, plastic; a means of creating suction for at least one built in cavity; a cavity for an insert-able device including an insert-able vibrator, an insert-able heater.

10. The wearable device according to claim 1 wherein said at least one entryway is at least in part inside said flexible body of faux flesh, having an open end and is aligned with a body orifice of the wearer, allowing at least one means of penetration to penetrate through said entryway and said body orifice of the wearer simultaneously.

11. The wearable device in accordance to claim 1 configured to be worn as a bra.

12. The wearable device in accordance to claim 11 further comprising at least one body made of a flexible material mimicking living human flesh, said body configured to at least in part mimic at least one human breast.

* * * * *